United States Patent
Virag et al.

(10) Patent No.: US 8,738,121 B2
(45) Date of Patent: May 27, 2014

(54) METHOD AND APPARATUS FOR DISTINGUISHING EPILEPTIC SEIZURE AND NEUROCARDIOGENIC SYNCOPE

(75) Inventors: Nathalie Virag, Cottens (CH); H. Toby Markowitz, Roseville, MN (US); Rolf Vetter, Neuchatel (CH)

(73) Assignee: Medtronic, Inc., Minneapolis, MN (US)

( * ) Notice: Subject to any disclaimer, the term of this patent is extended or adjusted under 35 U.S.C. 154(b) by 947 days.

(21) Appl. No.: 12/861,178

(22) Filed: Aug. 23, 2010

(65) Prior Publication Data
US 2012/0046558 A1 Feb. 23, 2012

(51) Int. Cl.
*A61B 5/0456* (2006.01)
*A61B 5/0205* (2006.01)

(52) U.S. Cl.
CPC ............. *A61B 5/0205* (2013.01); *A61B 5/0456* (2013.01)
USPC ....................................................... 600/521

(58) Field of Classification Search
CPC .......................... A61B 5/0205; A61B 5/0456
USPC ........................ 600/508–509, 519, 521, 544
See application file for complete search history.

(56) References Cited

U.S. PATENT DOCUMENTS

| | | | |
|---|---|---|---|
| 5,298,272 A | 3/1994 | Goodman et al. | |
| 5,501,701 A | 3/1996 | Markowitz et al. | |
| 5,720,294 A | 2/1998 | Skinner | |
| 5,857,978 A | 1/1999 | Hively et al. | |
| 5,928,272 A | 7/1999 | Adkins et al. | |
| 5,995,868 A | 11/1999 | Dorfmeister et al. | |
| 6,049,735 A | 4/2000 | Hartley et al. | |
| 6,304,775 B1 | 10/2001 | Iasemidis et al. | |
| 6,507,754 B2 | 1/2003 | Le Van Quyen et al. | |
| 6,658,287 B1 | 12/2003 | Litt et al. | |
| 2004/0215263 A1 | 10/2004 | Virag et al. | |
| 2007/0249954 A1 | 10/2007 | Virag et al. | |
| 2008/0269835 A1* | 10/2008 | Carlson et al. | 607/45 |
| 2010/0228103 A1* | 9/2010 | Schecter | 600/301 |

OTHER PUBLICATIONS

US 6,442,412, Aug. 27, 2002, Chance, (withrawn).
Attanasio, Antonia et al.; "An anorexic woman with convulsive loss of consciousness. Syncope or epileptic fits?"; International Journal of Cardiology; 116 (2007) e34-e38.
Hilz, M.J. et al.; "Decrease of sympathetic cardiovascular modulation after temporal lobe epilepsy surgery"; Guarantors of Brain; (2002), 125, 985-995.
Leutmezer, Fritz et al; "Electrocardiographic Changes at the Onset of Epileptic Seizures"; Epilepsia; 2003; 44 (3):348-354.
Mameli, O. et al.; "Autonomic nervous system activity and life threatening arrhythmias in experimental epilepsy"; Seizure; 2001; 10: 269-278.
Nei, Maromi et al.; "EEG and ECG in Sudden Unexplained Death in Epilepsy"; Epilepsia; 2004; 45(4):338-345.

(Continued)

*Primary Examiner* — Carl H Layno
*Assistant Examiner* — Jessica Anthony
(74) *Attorney, Agent, or Firm* — Michael C. Soldner

(57) ABSTRACT

A system and method for distinguishing an epileptic event from a syncope event that includes sensing a signal, generating sensed intervals in response to the sensed signal, generating an indication signal in response to an occurrence of an event, determining a marginality in response to the generated indication signal and the sensed intervals, and determining the event as being one of the epileptic event and the syncope event in response to the determined marginality.

23 Claims, 11 Drawing Sheets

(56) References Cited

OTHER PUBLICATIONS

Rugg-Gunn, Fergus J. et al.; "Cardiac Arrhythmias in focal epilepsy: a prospective long-term study"; Lancet; 2004; 364:2212-2219.

Sheldon, Robert et al.; "Historical Criteria That Distinguish Syncope From Seizures"; Journal of the American College of Cardiology; 2002; vol. 40. No. 1, 142-148.

Smith, D. et al.; "The misdiagnosis of epilepsy and the management of refractory epilepsy in a specialist clinic"; Q.J. Med; 1999; 92: 15-23.

Kouakam, Claude et al.; "Arrhythnmogenic Epilepsy: An Unusual Presentation of Recurrent Unexplained Syncope"; Heart Rhythm, vol. 2, No. 5, May Supplement 2005; s267-s268.

American Heart Association; Circulation, 1996;93: 1043-1065; http://circ.ahajournals.org/cgi/content/full/93/5/1043.

WebMD; "Implantable ECG Loop Recorder Differentiates Between Syncope and Epilepsy"; theheart.org; Sep. 9, 2009.

KTI/CTI The Innovation Promotion Agency; "Early warning system for syncopes and epilepsy"; Aug. 2006; pp. 1-6.

Vetter, Rolf et al.; "Observer of Autonomic Cardiac Outflow Based on Blind Source Separation of ECG Parameters"; IEEE Transactions on Biomedical Engineering; vol. 47, No. 5; May 2000; pp. 578-582.

Vetter, Rolf et al.; "Observer of the Human Cardiac Sympathetic Nerve Activity Using Noncausal Blind Source Separation"; IEEE Transactions of Biomedical Engineering; vol. 46; No. 3; Mar. 1999; pp. 322-330.

Wolber, Thomas et al.; Heart Obeys the Brain: Seizures Ceases Cardiac Rhythm; PACE; vol. 33; Aug. 2010; pp. e72-e75.

Zaidi, Amir et al.; Misdiagnosis of Epilepsy: Many Seizure-Like Attaches Have a Cardiovascular Cause; Journal of the American College of Cardiology; vol. 36; No. 1,; 2000; pp. 181-184.

Zijlmans, Maeike et al.; "Heart Rate Changes and ECG Abnormalities During Epileptic Seizures: Prevalence and Definition of an Objective Clinical Sign"; Epilepsia; 43(8):2002; pp. 847-854.

Devinsky, Orrin et al.; "Interictal Autonomic nervous System Function in patients with Epilepsy".

\* cited by examiner

METHOD AND APPARATUS FOR DISTINGUISHING EPILEPTIC SEIZURE AND NEUROCARDIOGENIC SYNCOPE

FIELD OF THE INVENTION

The present disclosure relates generally to medical devices, and more particularly to a method and apparatus for analyzing data to identify a recorded clinical event as being either a syncope event or a seizure event.

BACKGROUND

Syncope is a transient, self-limited loss of consciousness, usually leading to the patient falling due to global cerebral hypoperfusion. Cardiac arrhythmias associated with syncope include bradycardia, asystole, ventricular fibrillation and ventricular tachycardia. Epilepsy is one of several disorders that resemble syncope. While approximately half of adults may experience syncope, which is of neurocardiogenic origin, epilepsy, which is caused by a brain disorder, only occurs in about 1% of the population. Although the signs and symptoms of syncope and epileptic seizure are similar, treatment of seizures is directed to the brain, while treatment associated with syncope is directed to control of cardiac rhythm by use of medication, pacemaker, defibrillator, and/or ablation.

Epilepsy is frequently misdiagnosed. Recent estimates show that as many as 20% of patients diagnosed with epilepsy and undergoing long-term follow-up in hospital epilepsy clinics do not have epilepsy. Electrocardiogram (ECG) manifestation of epileptic seizures may not reveal an obvious diagnosis, as the spectra of responses from seizures and syncope overlap. Although an accurate patient history may help to distinguish syncope from seizures, this may require an observer to be present during an event. In addition, patients may experience amnesia following epilepsy or syncope events, further complicating gathering of an accurate history.

Providing an accurate indication to distinguish a seizure event from a syncope event will allow the physician treating the patient to direct appropriate further diagnostic work and treatment. Thus, a need exists to capture, record and distinguish syncope of cardiovascular origin from seizure of neurologic origin.

SUMMARY OF THE INVENTION

Recording and classifying cardiac electrical signals of a patient, before and/or during a patient event which may be a seizure or syncope, allows analysis and classification of the signals after the event. The electrical signals may be associated with cardiac pressure, motion, acceleration, and so forth. For example, according to an embodiment of the disclosure, distinguishing an epileptic event from a syncope event includes sensing a signal, generating sensed intervals in response to the sensed signal, generating an indication signal in response to an occurrence of an event, determining a marginality in response to the generated indication signal and the sensed intervals, and determining the event as being one of the epileptic event and the syncope event in response to the determined marginality. In one embodiment, classifying the event is accomplished by detecting R-waves from the patient, extracting R-R intervals from the detected R-waves, characterizing the R-R intervals in both a time period preceding the event, and in a time period encompassing the event, and comparing the R-R interval characteristics of the two time periods. A marginality of the R-R intervals of each of the two time periods is determined to classify the event as being a seizure event or syncope event.

In another embodiment, classifying the event is accomplished by detecting R-waves from the patient, extracting R-R intervals from the detected R-waves, characterizing the R-R intervals in a time period preceding the event, determining marginalities corresponding to predetermined intervals of the time period preceding the event, determining a maximum marginality of the determined marginalities, comparing the maximum marginality to a threshold, and determining the event as being one of the epileptic event and the syncope event in response to the comparing.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION OF THE INVENTION

Figure 1:
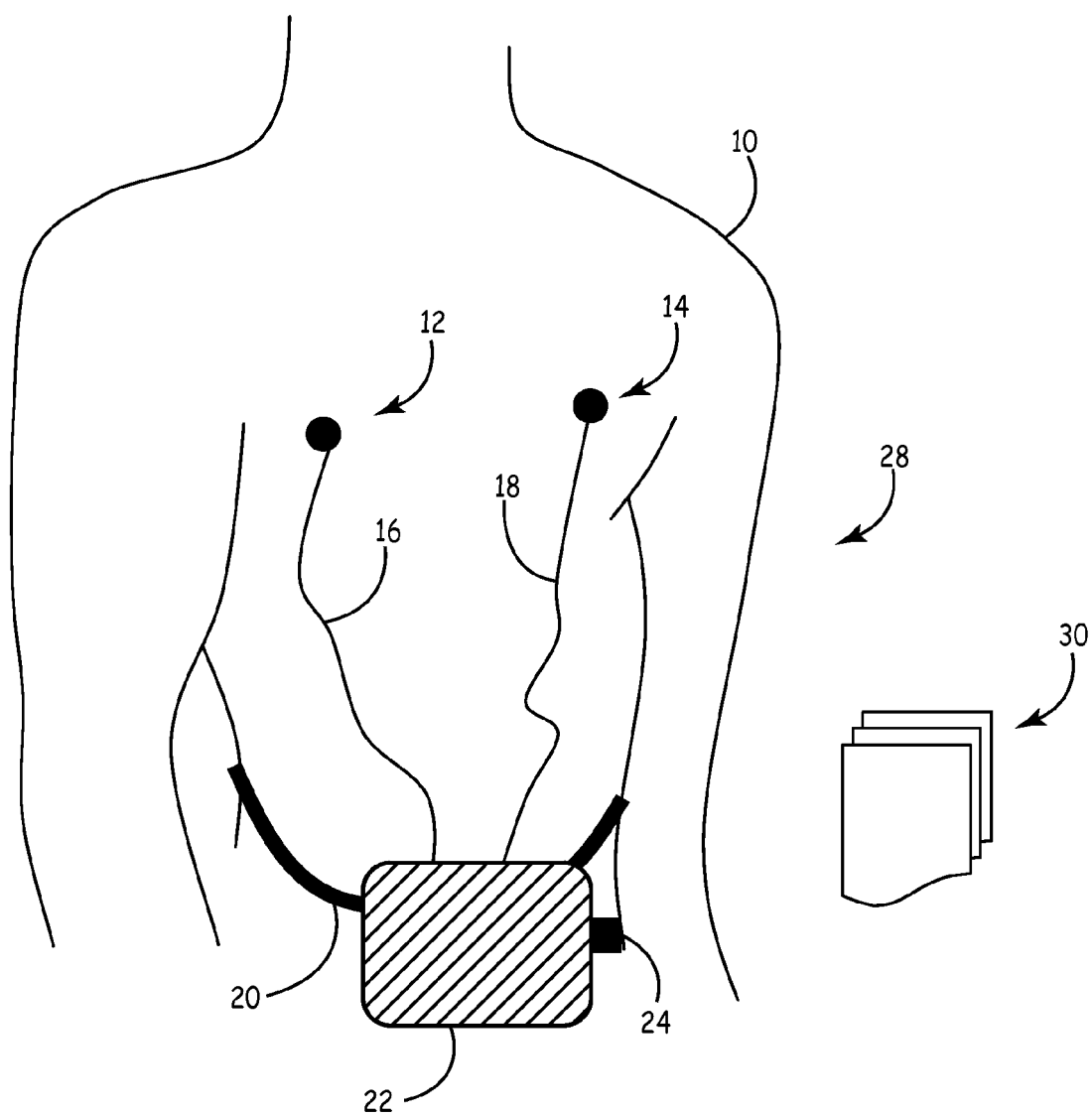
FIG. 1 is a schematic diagram of a monitoring device according to an exemplary embodiment of the disclosure.

FIG. 1 is a schematic diagram of a monitoring device according to an exemplary embodiment of the disclosure. As illustrated in FIG. 1, an external monitoring system may include an external monitor 22, supported by a belt 20 positioned around the waist of a patient 10. External monitor 22 incorporates an event indicator device, such as a button 24, which may be depressed by patient 10 or by a bystander (not shown) at the time of a patient event. During a monitoring period, patient 10 may record notes relating to palpitations, pre-syncope, lightheadedness, or other symptoms that are experienced by patient 10 into a diary 30 for later use by a user such as a physician, technician, nurse or the like. External monitor 22 is electrically coupled to patient electrodes 12, 14 via cables 16, 18. While electrodes 12, 14 are shown positioned along the chest of patient 10, electrodes 12, 14 may be attached to patient 10 in other anatomical positions (not shown) and therefore are not restricted to being positioned along only the chest area as illustrated. External monitor system 28 incorporates external monitor 22, belt 20, electrodes 12, 14 and cables 16, 18.

The signals received from patient electrodes 12, 14 are electrocardiogram-like. Whereas, the clinical use of the electrocardiogram (ECG) requires a specific relative position of ten electrodes on a patient, according to the present disclosure, two or more patient electrodes may be affixed to patient 10 and may be located in a variety of positions along patient 10. The signals received from patient electrodes 12, 14 correspond to those of an ECG and will be easily recognized by those skilled in the art.

Figure 2:
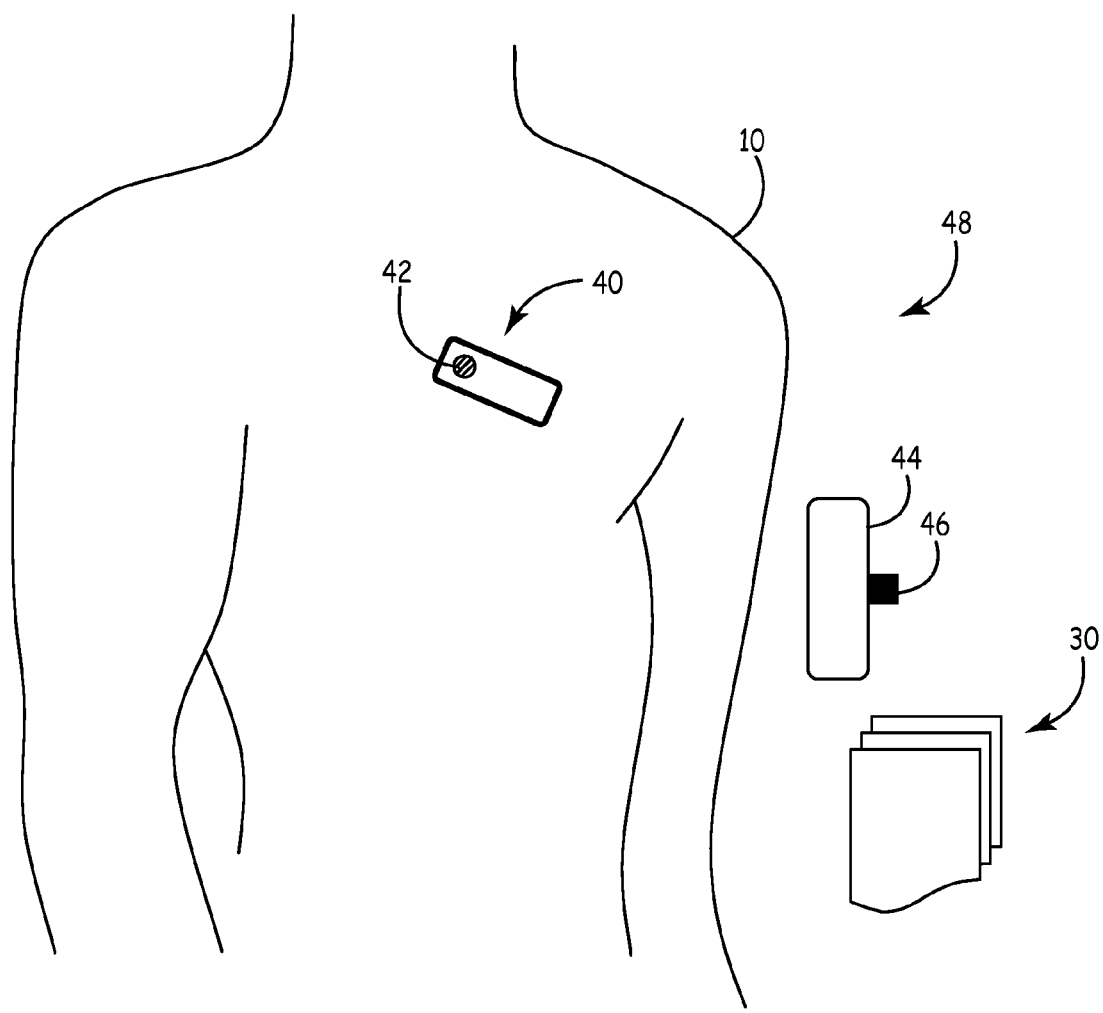
FIG. 2 is a schematic diagram of a monitoring device according to another exemplary embodiment of the disclosure.

FIG. 2 is a schematic diagram of a monitoring device according to another exemplary embodiment of the disclosure. As illustrated in FIG. 2, an implantable monitor system 48 may include an implantable monitor 40 that may be implanted below the skin of patient 10 to record data based on detection of electrocardiogram-like signals sensed via an electrode 42 implanted within patient 10. Electrode 42 may be incorporated within implantable monitor 40, or implanted to be positioned remotely from implantable monitor 40 and electrically coupled via a conductor (not shown). Implantable monitor system 48 incorporates implantable monitor 40 and a patient control 44 that includes an event indicator device, such as a button 46 positioned along patient control 44 that may be depressed by patient 10 or by a bystander (not shown) at the time of an event. During a monitoring period, patient 10 may record notes relating to palpitations, pre-syncope, lightheadedness, or other symptoms that are experienced by patient 10 in diary 30 for later use by a user such as a physician, technician, nurse or the like.

The electrocardiogram-like signals from electrode 42 may be detected and stored in implantable monitor 40, or may be processed and stored in a processed state in implantable monitor 40. Alternatively, either the electrocardiogram-like signals or the processed signals may be stored in patient control 44. Patient control 44 accompanies patient 10 throughout the period that patient 10 is being monitored, pending a patient event that may be either a syncope or a seizure event.

Figure 3:
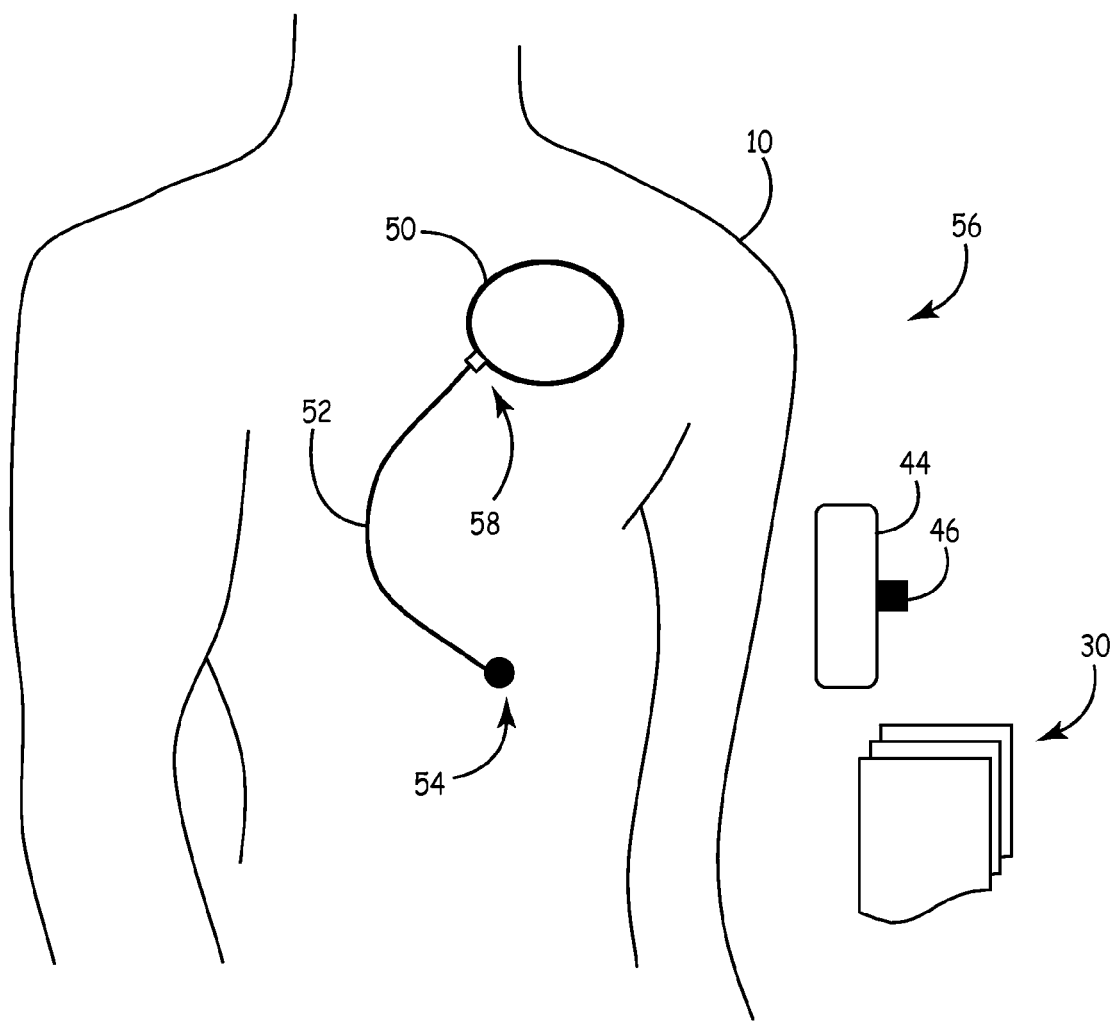
FIG. 3 is a schematic diagram of a monitoring device according to another exemplary embodiment of the disclosure.

FIG. 3 is a schematic diagram of a monitoring device according to another exemplary embodiment of the disclosure. As illustrated in FIG. 3, an implantable stimulator system 56 may include an electrode 54, a lead 52, a connector 58 and an implantable stimulator 50. For example, an implantable stimulator system may correspond to a cardiac rhythm management device, such as an implantable pacemaker, an implantable cardiac resynchronization device, a multi-chamber cardiac pacemaker, an implantable defibrillator, an implantable cardioverter defibrillator (ICD), or a combination of these devices. Implantable stimulator 50 is coupled to electrode 54 via connector 58 and lead 52. Electrode 54 may be positioned along the outside of the heart (not shown) of patient 10, along the inside of the heart (not shown) of patient 10, or may be implanted within the walls of the heart (not shown) of patient 10. Patient control 44 accompanies patient 10 throughout the period that patient 10 is being monitored pending a patient event, which may be either a syncope event or a seizure event. Button 46 may be depressed by patient 10 or by a bystander (not shown) at the time of an event. During a monitoring period, patient 10 may record notes relating to palpitations, pre-syncope, lightheadedness, or other symptoms that are experienced by patient 10 in diary 30 for later use by a user such as a physician, technician, nurse or the like.

It is understood that the present disclosure may be applied in any one or more of external monitor system 28, implantable monitor system 48 and implantable stimulator system 56 to gather data during an event that may be syncope or a seizure.

Figure 4:
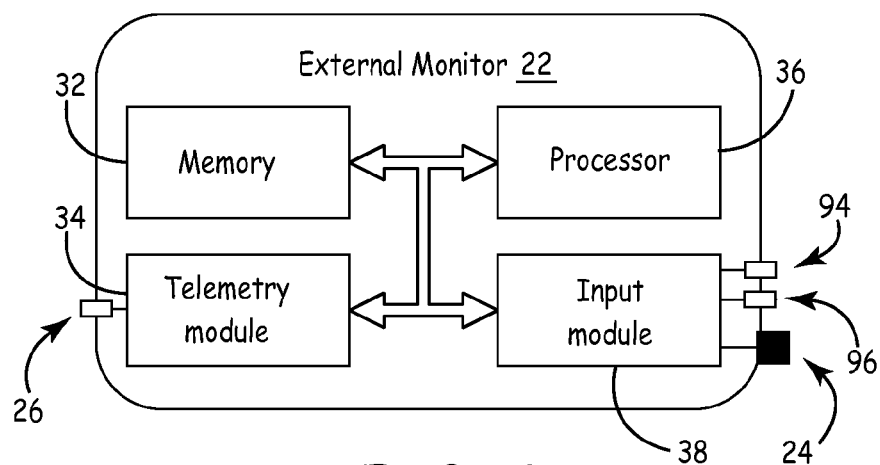
FIG. 4. is a functional block diagram of the monitoring device of FIG. 1.

FIG. 4 is a functional block diagram of the monitoring device of FIG. 1. As illustrated in FIGS. 1 and 4, external monitor 22 may include an input module 38 that is electrically coupled to button 24 to detect depression of button 24. Connectors 94, 96 are coupled to input module 38 for coupling to electrodes 12, 14 via cables 16, 18. Electrodes 12, 14 placed on the body of patient 10 sense cardiac electrical activity to generate a corresponding electrocardiogram (ECG) signal. The ECG signal contains signals which represent the depolarization of the various heart chambers. For example, depolarization of the ventricles of the heart is represented by an R-wave portion of ECG signal, as is known in the art.

Input module 38 receives the ECG signal and applies signal processing to detect the R-waves of patient 10. Various signal processing techniques may be applied to detect the R-waves, including the use of filters constructed in hardware, filters constructed in software, bandpass filters, notch filters, morphological wavelet filtering, and any other type of filter that may be applied for the detection of the R-waves. A processor 36 receives data from input module 38 and prepares the data for storage in a memory 32. A telemetry module 34 communicates with control unit 60 (described below and shown in FIG. 8) via wireless communication or directly via a cable 76 attached to connector 26 coupled to telemetry module 34. Telemetry module 34, memory 32, processor 36 and input module 38 share data and communicate with one another to receive signals from patient electrodes 12, 14, detect depression of button 24 and communicate data to external control unit 60.

Figure 5:
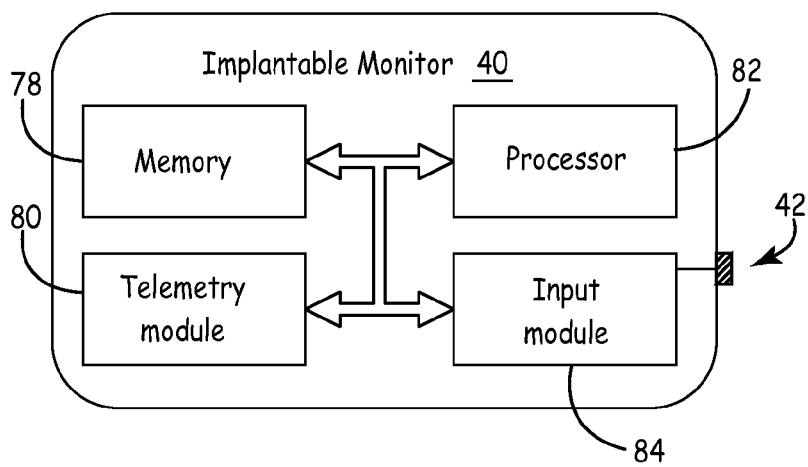
FIG. 5. is a functional block diagram of the monitoring device of FIG. 2.
Figure 8:
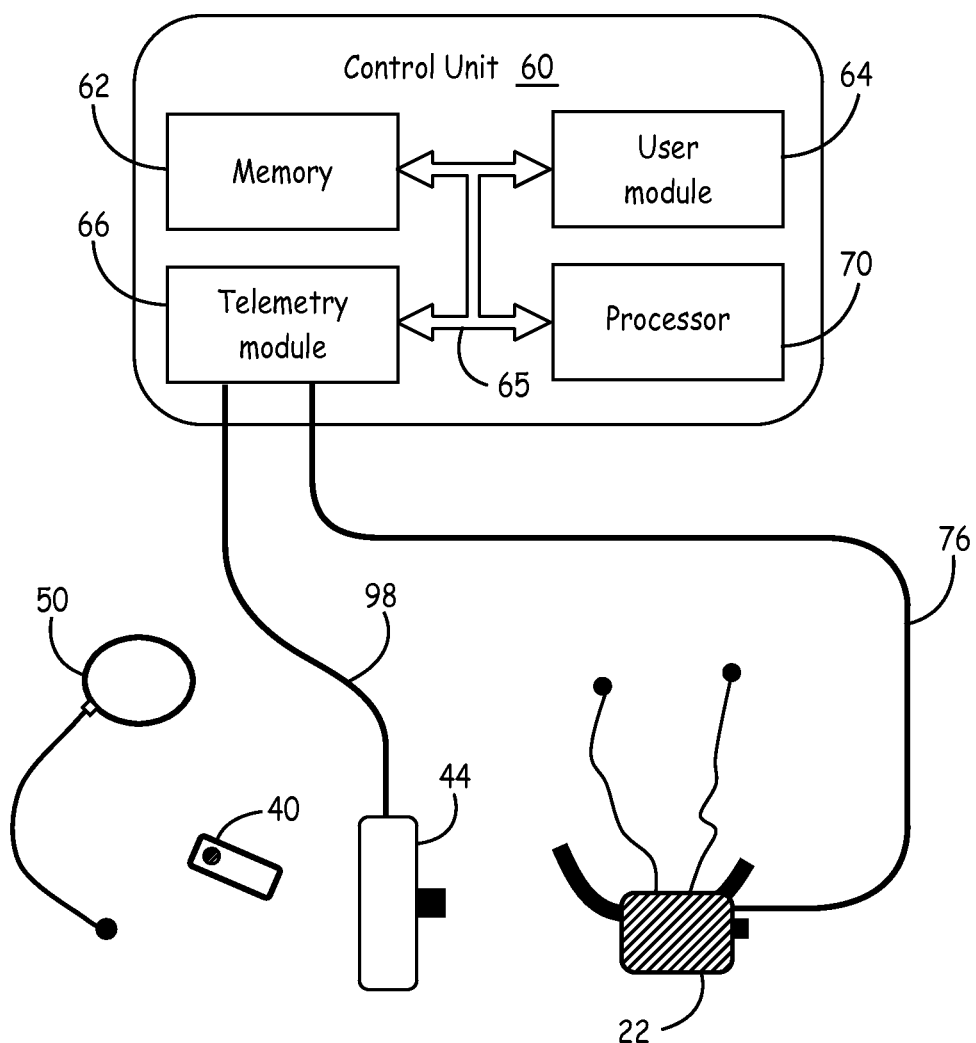
FIG. 8 is a block diagram of a control unit of a monitoring device system according to an exemplary embodiment of the disclosure.

FIG. 5 is a functional block diagram of the monitoring device of FIG. 2. As illustrated in FIGS. 2 and 5, an input module 84 of implantable monitor 40 is electrically coupled to implantable electrode 42. Input module 84 applies signal processing to the signal received from electrode 42 to detect the R-waves using techniques corresponding to those described above for external monitor 22 and as tailored for signals received by implantable electrode 42. While electrode 42 is positioned under the skin of patient 10 and electrodes 12, 14 are positioned along the outside of the skin, the techniques for signal processing and detecting the R-waves of patient 10 correspond to the techniques employed for external monitor 22. A processor 82 receives data from input module 84 and prepares the data for storage in a memory 78. A telemetry module 80 communicates with control unit 60 (described below; FIG. 8) via wireless communication and with patient control 44 via wireless communication. Telemetry module 80, memory 78, processor 82 and input module 84 share data and communicate with one another to receive signals from patient electrode 42. When button 24 is depressed, patient control 44 wirelessly communicates the depression to implantable monitor 40.

Figure 6:
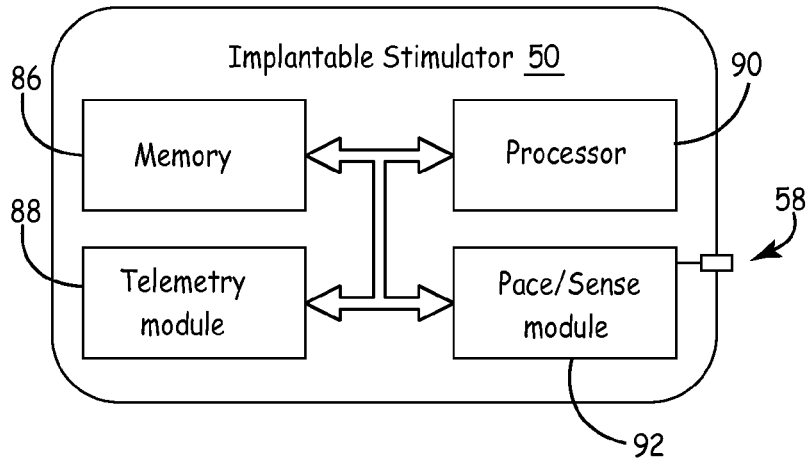
FIG. 6 is a functional block diagram of the monitoring device of FIG. 3.

FIG. 6 is a functional block diagram of the monitoring device of FIG. 3. As illustrated in FIGS. 3 and 6, implantable stimulator 50 may include a pace/sense module 92 that is coupled to electrode 54 via lead 52 and connector 58. Pace/Sense module 92 applies signal processing to the signal from electrode 54 for detection of the R-waves with techniques corresponding to those described above for external monitor 22 and implantable monitor 40. While electrode 54 is positioned within or along the heart of patient 10, and electrodes 12, 14 are on the outside of the skin, the techniques for signal processing and recovering the R-waves of patient 10 correspond with those described above for external monitor 22. A processor 90 receives data from pace/Sense module 92, notes the time of detection and prepares the data for storage in memory 86. A telemetry module 88 communicates with control unit 60 (described below and shown in FIG. 8) via wireless communication and with patient control 44 via wireless communication. Telemetry module 88, memory 86, processor 90 and pace/sense module 92 share data and communicate with one another to receive signals from patient electrode 54. When button 24 is depressed on patient control 44, patient control 44 wirelessly communicates the depression to implantable stimulator 50. Pace/sense module 92 incorporates components and circuitry to sense cardiac electrical activity, such as depolarizations of the heart. Pace/sense module 92 may also incorporate components and circuitry to pace the heart, to perform cardioversion of the heart and to perform defibrillation of the heart.

Figure 7:
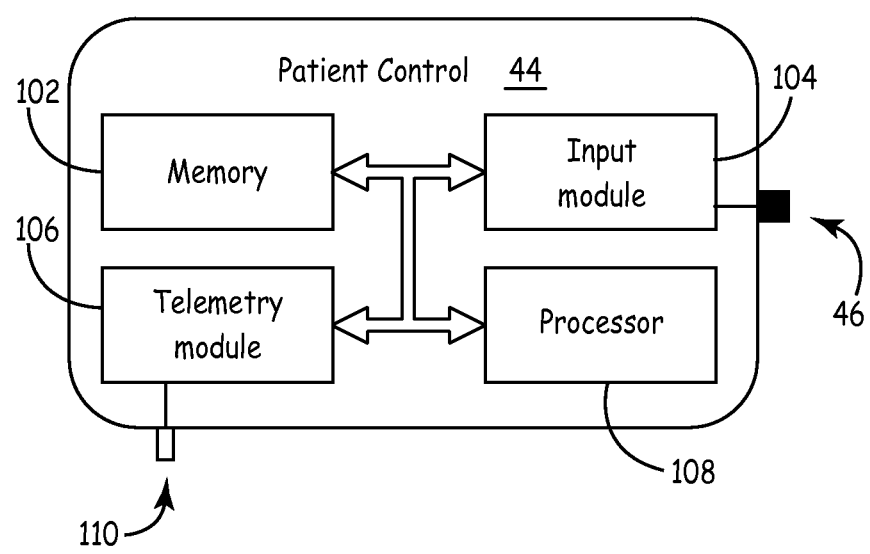
FIG. 7 is a block diagram of a patient control utilized in a monitoring device according to an exemplary embodiment of the disclosure.

FIG. 7 is a block diagram of a patient control utilized in a monitoring device according to an exemplary embodiment of the disclosure. As illustrated in FIG. 7, patient control 44 incorporates memory module 102, input module 104, telemetry module 106, processor module 108, button 46 and connector 110, which is electrically coupled to telemetry module 106. Memory module 102, input module 104, telemetry module 106 and processor module 108 share data and communicate with one another as shown. Button 46 may be depressed by patient 10 or by a bystander to signal a patient event which may be syncope or a seizure. Upon depression of button 46, patient control 44 records the time of the button depression for later transmission to control unit 60 via telemetry module 106 either wirelessly or via connector 110 and cable 98 (see FIG. 8).

FIG. 8 is a block diagram of a control unit according to an exemplary embodiment of the disclosure. As illustrated in FIG. 8, a control unit 60 communicates with one or all of the external monitor 22, the implantable monitor 40, the implantable stimulator 50, and a patient control 44. For example, control unit 60 communicates wirelessly with one or both implantable stimulator 50 and implantable monitor 40 via a telemetry module 66. One or both of external monitor 22 and patient control 44 may communicate either wirelessly with control unit 60 via telemetry module 66, or directly via a direct wire communication such as a cable 76 or a cable 98, respectively, coupled with telemetry module 66. Communication between one or more of implantable monitor 40 and implantable stimulator 50 and control unit 60 typically is performed via a wireless connection via telemetry module 66. In this way, patient data may be communicated to control unit 60 through telemetry module 66 from one or more of implantable stimulator 50, implantable monitor 40, patient control 44 and external monitor 22.

A user module 64 allows a user, such as a physician, a nurse, or a technician, for example, to review the data input by patient 10, to input information, such as the time of the patient event or other information input within patient diary 30, as described above. User module 64 enables the user to input data and provides output for review by the user, including but not limited to a visual display, an electronic output and a printed output from control unit 60. Control unit 60 indicates the classification (described below) of a patient event via user module 64. Within control unit 60, communication between a memory 62, a user module 64, a telemetry module 66 and a processor 70 takes place via a data bus 65, as illustrated. While these four modules are shown within control unit 60, control unit 60 may be constructed as separate units with various combinations of the four modules. For example, memory 62 and processor 70 could be combined within one unit and connected to user module 64 and telemetry module 66 in another unit. Processor 70, memory 62 and user module 64 could utilize off-the-shelf hardware for the construction of control unit 60.

Figure 9:
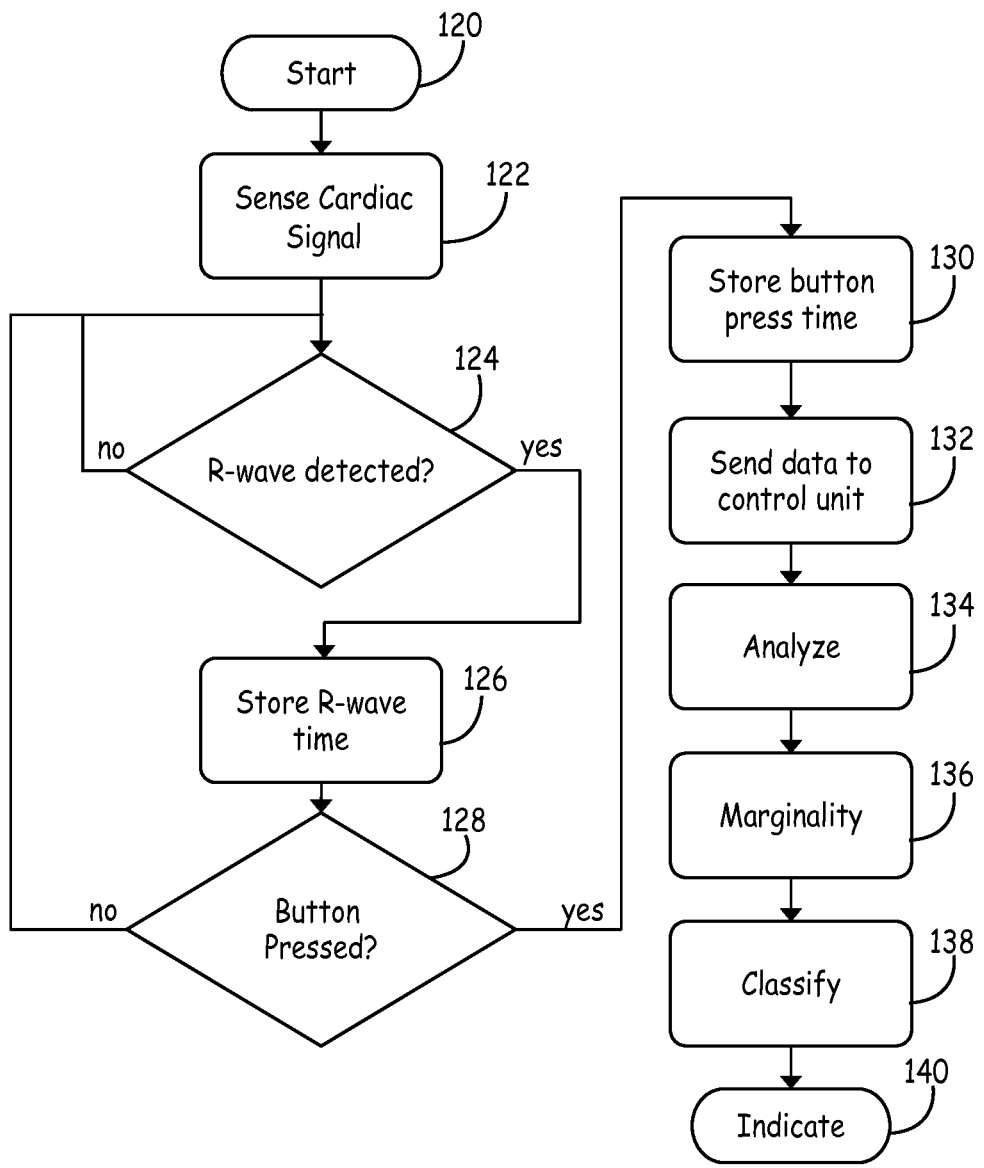
FIG. 9 is a flow chart of recording of patient event data and classification of the event using a monitoring device according to an exemplary embodiment of the disclosure.

FIG. 9 is a flow chart of recording of patient event data and classification of the event using a monitoring device according to an exemplary embodiment of the disclosure. As illustrated in FIG. 9, patient 10 records data, such as activities and symptoms experienced prior to and during experiencing an event, where the event is expected to be either syncope or a seizure. A monitoring device, such external monitor 22, implantable monitor 40, or implantable stimulator 50 senses cardiac electrical activity to generate a corresponding electrocardiogram (ECG) signal, Block 122. The monitoring device identifies R-waves associated with the sensed signal, Block 124, and when an R-wave is detected, Yes in Block 124, the time and date of the R-wave detection are stored, Block 126. While the actual date and time may be stored, various alternatives may be substituted with regards to conserving memory storage space. These alternatives include storing an initial time and then subsequently storing a time increment from the initial time for subsequent R-waves, and noting the time the recording was started in the patient's diary and only recording a time increment from the time the recording was begun. In addition to storing the time the R-wave was detected, Block 126, a determination is made as to whether the event indicator, i.e., button 24 or button 46 described above, for example, has been depressed, Block 128, indicating a patient event occurred. If the button has not been depressed, No in Block 128, the process continues to Block 124 where the system waits for the next R-wave to be detected.

Once depression of the button has occurred, either by the patient, or by a bystander, for example, when the patient is unable to depress the button, Yes in Block 128, the date and time of the button depression is stored, Block 130. The stored data is subsequently transmitted to telemetry module 66 in control unit 60, Block 132, as described above. The data transmission between the monitoring device and control unit 60 via telemetry module 66 may be wireless or via cable 76, 98. The data transmitted to control unit 60 is analyzed, Block 134, and a marginality is determined from the recorded data, Block 136, as described below. The patient event is classified based on the computed marginality, Block 138, and control unit 60 indicates the event as corresponding to either a syncope event or a seizure event based on the determined marginality, Block 140, as will be described below in detail.

Figure 10:
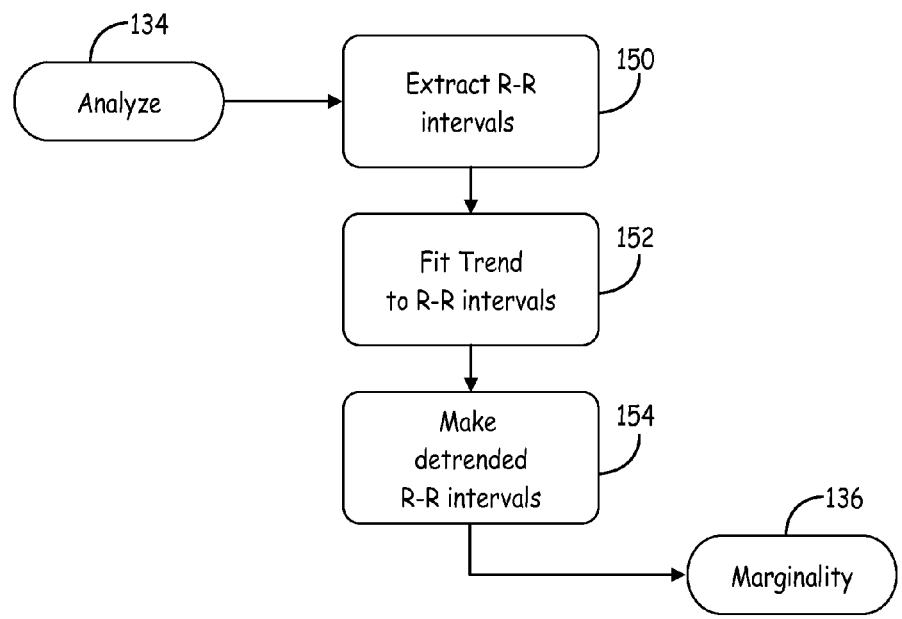
FIG. 10 is a flow chart of determining of an R-R extraction and removing of trend function for distinguishing an epileptic seizure and syncope, according to an embodiment of the disclosure.

FIG. 10 is a flowchart of determining of an R-R extraction and removing of trend function for distinguishing an epileptic seizure and syncope, according to an embodiment of the disclosure. As illustrated in FIG. 10, during analysis of the data by the control unit 60, Block 134 of FIG. 9, the data including the detected R-wave time data and the time of the button depression are processed to extract the detected R-R intervals, the intervening time interval between subsequently detected R-waves. When the heart is in a normal rhythm, the detected R-R intervals reflect the period that corresponds to the heart rate. Heart rate measured in beats per minute is the frequency of heart contractions. Period is the reciprocal of frequency. When the heart beats irregularly, the inter-beat interval, the detected R-R interval, will fluctuate between beats. When measured over many beats, the fluctuations may not be evident or as evident as observed on a beat by beat basis. According to one embodiment of the disclosure, for example, the detected R-R intervals are extracted by calculating the successive differences of the recorded R-wave times imported from external monitor 22, implantable monitor 40 and implantable stimulator 50. The total time of the recording is noted as the time difference between the time of the button depression (imported as described above, along with the R-wave times) and the time of the first recorded R-wave.

A trend function is fit to the extracted R-R intervals, Block 152. The trend function, which may be a line or a curve, is a third-order polynomial trend function generated from the R-R interval data, and varies over time with values corresponding to the time of each detected R-R interval in the data. The trend function corresponds to variations in R-R intervals that occur as a result of normal fluctuations in daily activities of the patient. A set of detrended R-R intervals is created to reduce the effect of these normal fluctuations in heart rate by removing the trend function from the R-R intervals, Block 154. The process continues using the detrended R-R intervals to compute a marginality, Block 136 of FIG. 9.

Figure 11:
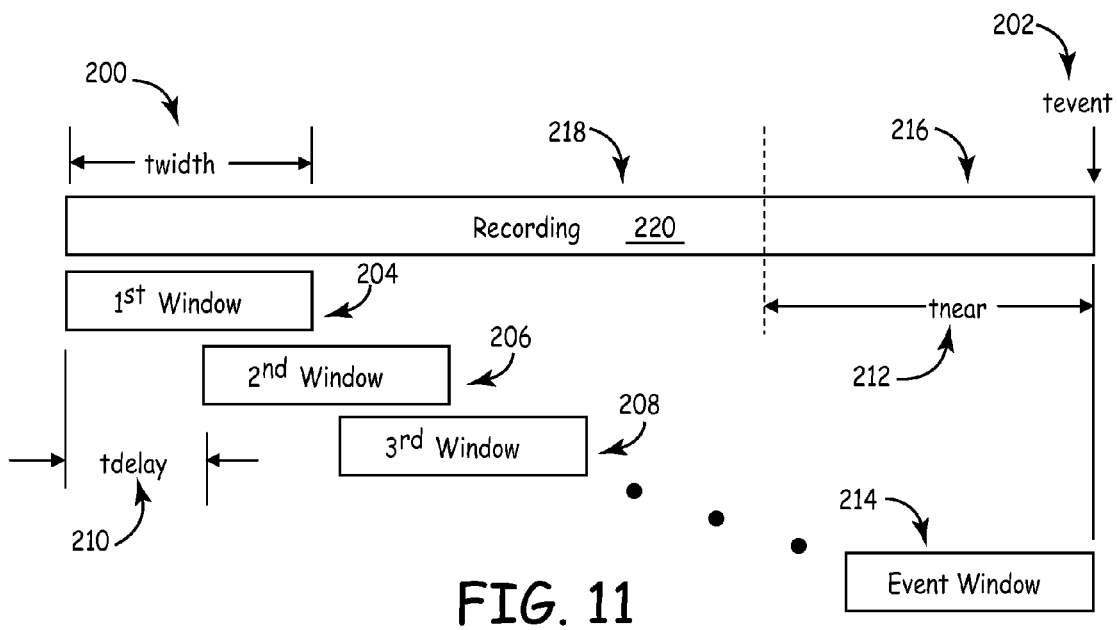
FIG. 11 is a graphical representation illustrating the use of time windows for computing marginality of detected R-R intervals for distinguishing an epileptic seizure and syncope, according to an embodiment of the disclosure.

FIG. 11 is a graphical representation illustrating the use of time windows for computing marginality of detected R-R intervals for distinguishing an epileptic seizure and syncope, according to an embodiment of the disclosure. Marginality is a measure of the frequency of occurrence of marginal beat-to beat heart interval fluctuation, which is utilized as a marker of whether a patient event was syncope or a seizure. As illustrated in FIG. 11, recording 220 is performed, as described above in FIG. 9, from the time of sensing cardiac signals, Block 122, and detecting R-waves, Block 124, until button 24, 46 is depressed, Yes in Block 128, indicating the patient is experiencing occurrence of an event. The data are analyzed according to time windows. Event window 214 is placed so the trailing, right-hand, edge aligns with the depression of button 24, 46 at time tevent 202. Windows are successively placed from event window 214 in reverse time to the beginning of the recording. The first window 204 is the window that contains the first detected R-waves after instructing the patient and beginning the recording 220. The second window 206 begins time tdelay 210 after the beginning of first window 204. Time window width, twidth 200 is nominally 6 minutes although twidth 200 of lesser and greater amounts may be used; twidth 200 up to 10 minutes may be useful in some settings. The last window of the recording, event window 214 terminates at the time of the event noted by patient 10 as measured by the time of the depression of button 24, 46 and identified as tevent 202. If time tdelay 210 is set to less than twidth 200, the windows are said to overlap. As illustrated in FIG. 11, overlap occurs when the data in second window 206 contains some of the same data as in first window 204. On the other hand, if time tdelay 210 were set equal to time twidth 200, the windows would not overlap and the data would be uniquely contained in each window. Time tdelay 210 is not greater than time twidth 200 and nominally is set equal to twidth 200.

Figures 12, 13:
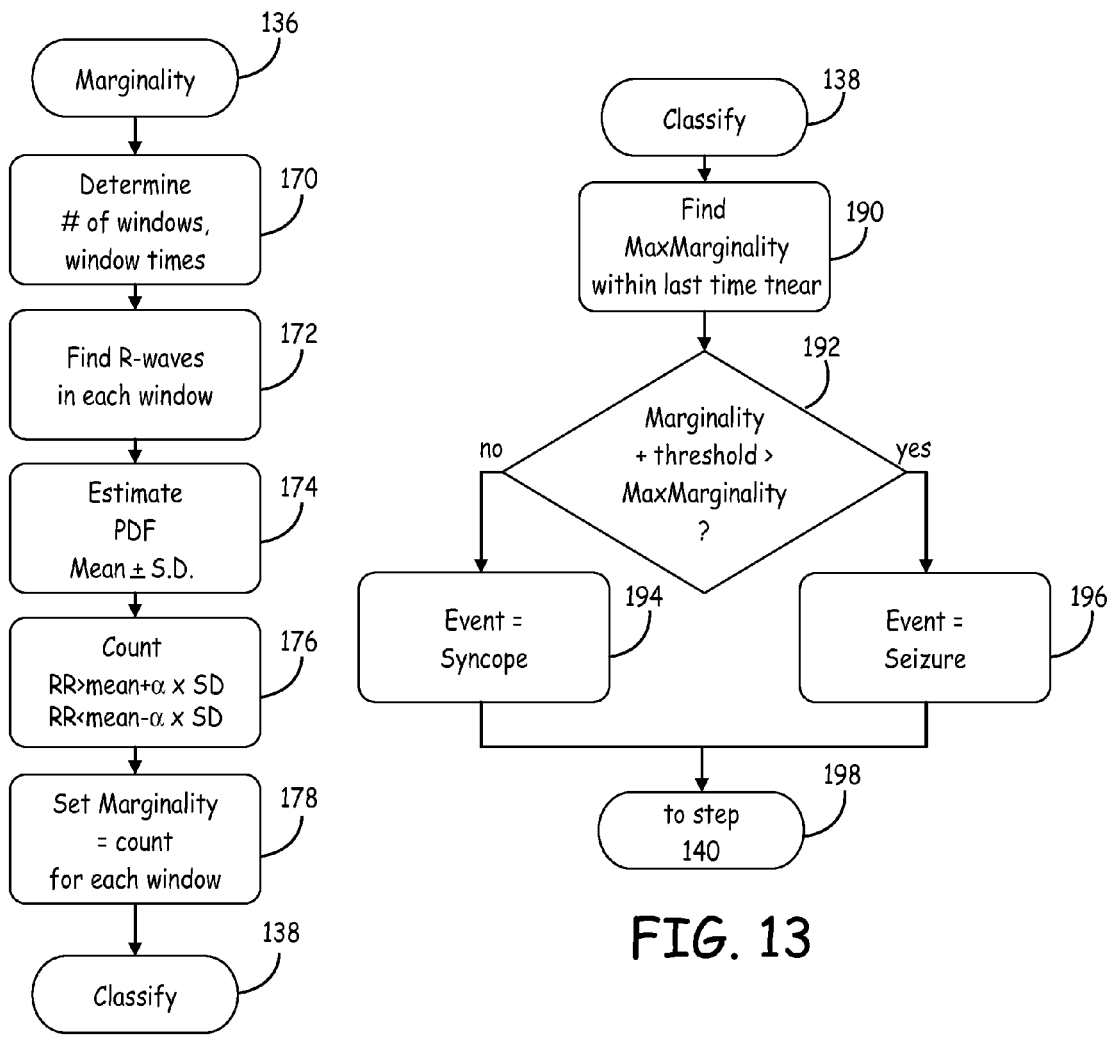
FIG. 12 is a flow chart of determining of a marginality for distinguishing an epileptic seizure and syncope in a monitoring device according to an embodiment of the disclosure.
FIG. 13 is a flow chart of a classification of an event as one of an epileptic seizure event and a syncope event, according to an embodiment of the disclosure.

FIG. 12 is a flowchart of determining of a marginality for distinguishing an epileptic seizure and syncope in a monitoring device according to an embodiment of the disclosure. As illustrated in FIG. 12, according to an embodiment of the disclosure, during the determination of marginality, Block 136 of FIG. 9, which is a measure of the frequency of occurrence of marginal beat-to beat heart interval fluctuations utilized as a marker of whether a patient event was syncope or a seizure, the number of windows and the times associated with the beginning and ending of each window are calculated, Block 170. For example, the first detected R-wave within each window and the last detected R-wave within each window are identified along with the intervening detected R-waves that fall into each window, Block 172. The total number of detected R-waves within each window is counted and stored for later use. R-R intervals are then determined from the identified first detected R-wave, last detected R-wave and intervening R-waves, and then detrended as described above. A probability density function (PDF) is estimated for each window of the series of detrended R-R intervals, Block 174.

Figure 14:
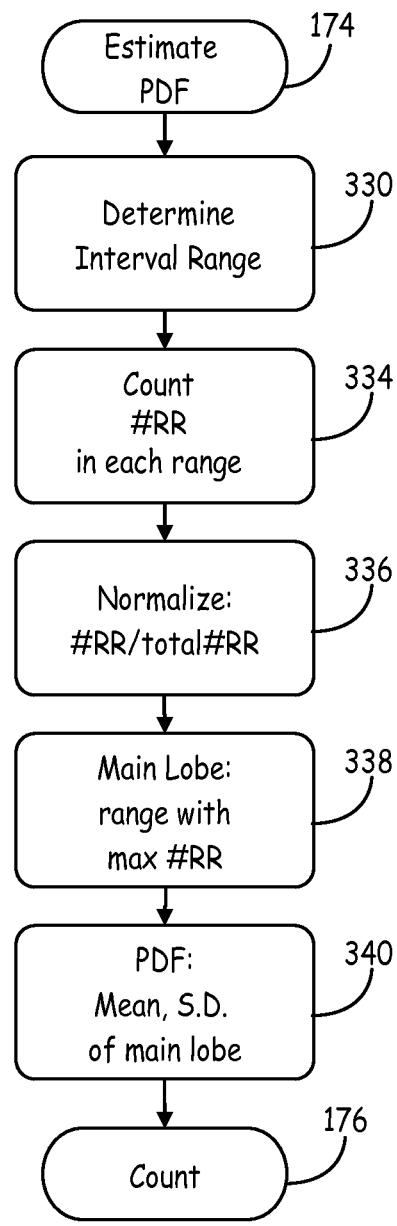
FIG. 14 is a flow chart of determining an estimation of a probability density function of R-R intervals in a given window of detected R-waves, according to an embodiment of the disclosure.

FIG. 14 is a flowchart of determining an estimation of a probability density function of R-R intervals in a given window of detected R-waves, according to an embodiment of the disclosure. During the estimation of a probability density function corresponding to the R-R intervals for each window, Block 174 of FIG. 12, an interval range is determined, Block 330. For example, in order to determine the interval range, each of the detrended R-R intervals identified in a given window is examined to determine a minimum detrended R-R interval and a maximum R-R interval associated with the window, Block 330. A constant, N, which corresponds to the number of equal interval ranges to be evaluated for each window is selected. According to one embodiment, constant N may range from 10 to 30, and is nominally selected to be 20. A smaller value of N results in larger interval ranges and, possibly, a larger number of detected R-R intervals may fall within each interval range. The width of each interval range is calculated as a quotient of the difference between the maximum detrended R-R interval and the minimum detrended R-R interval, divided by the constant N, i.e., (max-min)/N. The first of the series of N interval ranges extends from the minimum detected R-R interval to the minimum detected R-R interval plus the quotient. The last of the series of extends from the maximum detected R-R interval minus the quotient (max-min)/N to the maximum detected R-R interval. Thus, there are N equal interval ranges extending from the minimum detected R-R interval to the maximum detected R-R interval.

In another embodiment, during determination of the interval range, Block 332, the detrended R-R intervals are not examined to find the minimum detrended R-R interval and the maximum detrended R-R interval. Rather, N interval ranges are set to extend between an interval of 0.25 seconds and an interval of 2.0 seconds corresponding to a heart rate range from 30 to 240 beats per minute. Setting the interval ranges in this manner yields more robust results, especially for patients with limited variability of the R-R intervals. The use of fixed interval ranges simplifies the computational requirements for the system.

According to an embodiment of the disclosure, the N interval ranges may be individualized to each patient. That is, the N interval ranges may extend between a minimum interval and a maximum interval that are established for each patient. The choice of the number N of interval ranges is dependent on the width of the analysis window and the number of R-R intervals that are within the window. According to an embodiment of the disclosure, the N interval ranges are determined by setting N equal to the square root of the number of R-R intervals within each analysis window, so that the value of N, i.e., the N interval ranges utilized, will be dependent on the heart rate of the patient, for example, Once the interval range is determined, the total number of detected R-R intervals that fall within each interval range is counted, Block 334. Since each detected R-R interval corresponds to a detrended R-R interval, the total number of detected R-R intervals is equivalent to the total number of detrended R-R intervals. The number of detected R-R intervals is equal to the number of detected R-waves in all windows except the first window; in the first window, there is one less detected R-R interval than the number of detected R-waves. It is simpler to refer to the total number of detected R-R intervals, although one could substitute the total number of detrended R-R intervals in these steps and achieve the same result. The number of R-R intervals within each range is normalized, Block 336, by dividing the number of detected R-R intervals within each range by the total number of detected R-R intervals.

The normalized number of detected R-R intervals that fall within each interval range is a distribution. The distribution is the frequency of detrended R-R intervals within each interval range. Displayed graphically, the distribution appears as a histogram. The main lobe of the histogram falls on the interval range for which the largest number of detected R-R intervals that occur within a particular window. When the patient is in a normal rhythm such as normal sinus rhythm, the main lobe of the histogram represents the patient's normalized heart rate and includes the physiologic variation in heart rate such as accompanies the patient's respiration or the baroreflex regulation of blood pressure. When the patient has extrasystolic activity, the side lobes reflect the extrasystolic activity and pauses that may result from such activity. The main lobe of the histogram is identified and examined. The main lobe of the histogram for each window consists of the interval range from each window that includes the greatest number of detected R-R intervals, Block 338. A mean and a standard deviation (S.D.) are calculated on the distribution of detected R-R intervals that fall within the main lobe of each window, Block 340. The detected R-R intervals that fall within the main lobe of each window are those detected R-R intervals that lie within the interval range of the main lobe.

Returning to FIG. 12, a marginality is calculated for each window, based on the detected R-R intervals within each window. Each detected R-R interval is compared with the mean of the PDF and the standard deviation of the PDF at the time of the detected R-R interval. The number of the R-R intervals whose values are outside a marginality interval defined by the mean of the PDF plus and minus a constant $\alpha$ (alpha) times the standard deviation of the PDF at the time of each detected R-R interval is determined, Block 176, and the number of R-R intervals determined to be outside the marginality interval for each window is used to determine the marginality, Block 178. The process continues in step 138 to classification of the patient event based on the determined marginality. The value of the constant $\alpha$ (alpha) is nominally about 1.96, however, the value of this constant may be from 1.5 to 4.0. The value of the constant $\alpha$ (alpha) may be adjusted by the user to adjust the sensitivity and specificity of the system according to the experience and preferences of the user, where the user is a physician, a technician, a nurse, or other individual involved in the application of the system and analysis of the data.

FIG. 13 is a flowchart of classification of an event as one of an epileptic seizure event and a syncope event, according to an embodiment of the disclosure. As illustrated in FIG. 13, in order to classify the event as one of an epileptic seizure and syncope, a maximum of the marginality data, MaxMarginality, within time tnear 212 (see FIG. 11) of patient event, tevent 202 is determined, Block 190. Time tnear 212 defines a time period 216 prior to the indicated time of the event, tevent 202, over which a maximum is obtained for comparison to marginality computations of a prior time period 218. Time tnear 212, if set equal to zero, results in MaxMarginality being equal to the marginality calculated at tevent 202, the time of the patient event. If time tnear 212 is set greater than zero, for example 30 minutes, a maximum marginality, MaxMarginality, is determined for prior time period 216 from 30 minutes prior to tevent 202 until tevent 202. According to an embodiment of the disclosure, time tnear 212 may be set to be in the range from approximately 30 minutes to 2 hours.

Once the maximum marginality, MaxMarginality, is determined in Block 190, the maximum of the marginality of each window plus a pre-determined threshold is compared to the MaxMarginality, Block 192. The pre-determined threshold is used to ensure the marginality comparison of windows that are not within time tnear 212 of tevent 202 are significantly greater than the MaxMarginality. For example, the pre-determined threshold may be a fixed value, or may be a percentage of the MaxMarginality. In one embodiment, the predetermined threshold is be selected to be a product of the MaxMarginality and a constant, such as is 0.1 (i.e. 10 percent), for example.

If the sum of the marginality and the predetermined threshold for any window of prior period 218 is greater than the MaxMarginality determined for the time window including indication of the occurrence of the event, time tnear 212, the patient event is determined to be an epileptic seizure event, Block 196. If no window of prior period 218 has a maximum greater than the MaxMarginality, the patient event is determined to be syncope event, Block 194.

Once the determination has been made that the event is a seizure event, Block 196, or that the event is a syncope event, Block 194, control unit 60 indicates the classification to a user via user module 64 using an electronic signal, a printed output, a visible display, a computer display or an aural announcement to perform the indication to the user. In addition to the indicating the classification of the event, control unit 60 may also provide the times of the detected R-waves, the detected R-R intervals, the marginality for each window, the time the monitoring was started and the time of depression of button 24, 46.

Figure 15:
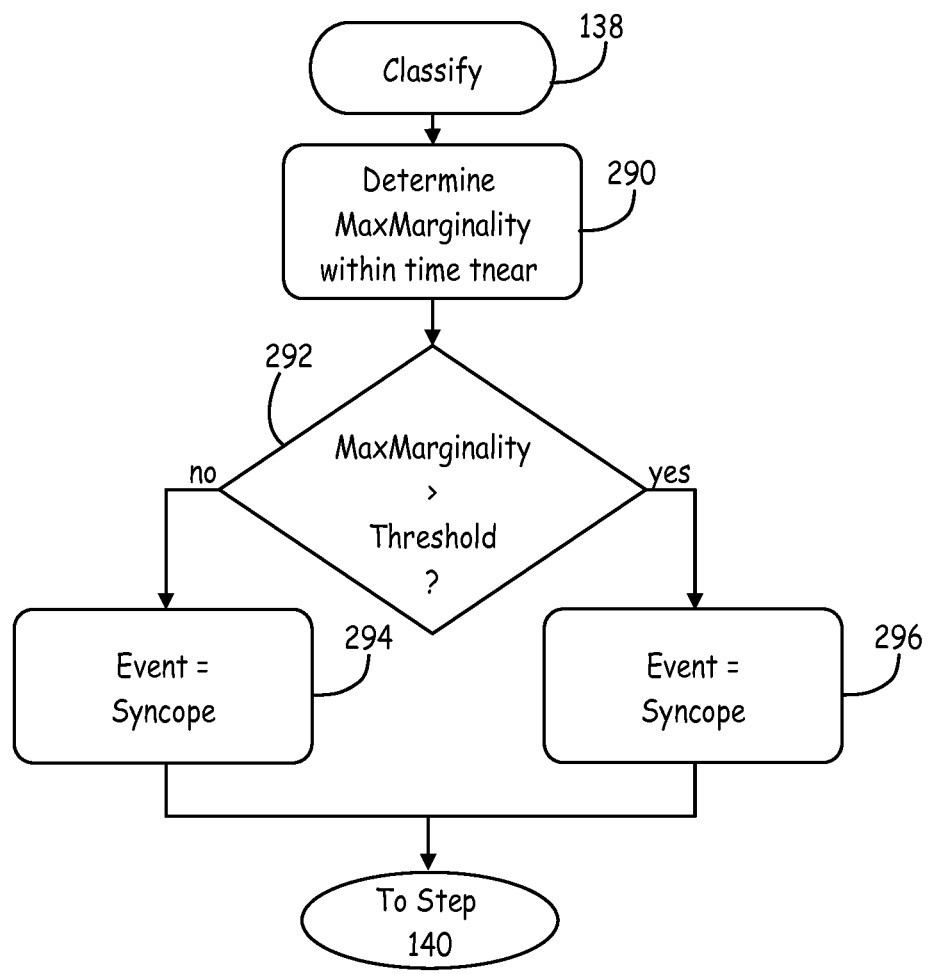
FIG. 15 is a flowchart of classification of an event as one of an epileptic seizure event and a syncope event, according to an embodiment of the disclosure.

FIG. 15 is a flowchart of classification of an event as one of an epileptic seizure event and a syncope event, according to an embodiment of the disclosure. As illustrated in FIG. 15, in order to classify the event as one of an epileptic seizure and syncope, a maximum of the marginality data, MaxMarginality, within the predetermined time period prior to the indication of the occurrence of the event, time tnear 212 (see FIG. 11) of patient event, tevent 202, is determined, Block 290. In particular, according to the embodiment illustrated in FIG. 15, for each of the intervals of time period 216, the number of R-R intervals having values that are outside the marginality interval, described above in reference to FIG. 12, for example, is determined. This determined number of R-R intervals outside the marginality interval is then divided by the total number of R-R intervals that are within the given window to generate a percentage for that window.

The maximum determined percentage for all of the determined intervals is then set as the MaxMarginality. A determination is made as to whether the MaxMarginality is greater than a predetermined epilepsy threshold, Block 292. According to an embodiment of the disclosure, if marginality is determined as a percentage, the epilepsy threshold may also be a percentage, such as four percent, for example.

If the MaxMarginality is greater than the predetermined epilepsy threshold, YES in Block 292, the patient event is determined to be an epileptic seizure event, Block 296. If the MaxMarginality is not greater than the predetermined epilepsy threshold, NO in Block 292, the patient event is determined to be syncope event, Block 294.

The data that are required to arrive at a classification of a patient event as a seizure or syncope may be stored or processed in various elements described above. The raw electrocardiographic signals received from patient electrodes may be stored for later processing. However, the limitations as to the amount of power and size required for such storage may dictate a design in which processing of data and subsequent storage is more practical. The data may be processed beyond the extraction of the times of the R-wave detections and then stored for further analysis. It is possible the complete evaluation of the entire record is carried out in real time with an update as more data are gathered. In this manner, the classification of the event as to whether the patient event is a seizure or syncope could be available just moments after a patient event.

Additional embodiments are envisioned in which the data are communicated to patient control 44 for storage and/or processing. Patient control 44 is described, above, as accompanying patient 10 while patient 10 is being monitored. External monitor 22 could also communicate with patient control 44. Any of the devices used for gathering the patient electrical signals, external monitor 22, implantable monitor 40, and implantable stimulator 50 could communicate to patient control 44 on a regular basis and process the data to analyze, classify and indicate whether the patient event is a seizure or syncope. Patient control 44 then communicates information to control unit 60 for output to the user. Patient control 44 could also communicate directly to the user. Any of the external monitor 22, the implantable monitor 40, the patient control 44 and the control unit 60 may communicate to the user with the indication of a seizure or syncope for a patient event. For prolonged recording of patient data, especially in the event that patient events are rare and infrequent, the recording device may discard data on a daily basis so as to not burden the memory storage requirements of a patient device.

Some of the techniques described above may be embodied as a computer-readable medium comprising instructions for a programmable processor such as processor 36, 70, 82, 90 or 108 shown in FIGS. 4-8, for example. The programmable processor may include one or more individual processors, which may act independently or in concert. A "computer-readable medium" includes but is not limited to any type of computer memory or volatile or non-volitile media such as floppy disks, conventional hard disks, RAM, ROM, CD-ROM, NVRAM, EEPROM, flash memory, and the like, along with a magnetic or optical storage medium. The medium may include instructions for causing a processor to perform any of the features described above for distinguishing an epileptic event from a syncope event according to the present disclosure. The instructions may be implemented as one or more software modules, which may be executed by themselves or in combination with other software While a particular embodiment of the present invention has been shown and described, modifications may be made. It is therefore intended in the appended claims to cover all such changes and modifications, which fall within the true spirit and scope of the invention.

The invention claimed is:

1. A medical device system to distinguish an epileptic event from a syncope event, the medical device system comprising:

a monitoring device to sense a signal and generate sensed intervals in response to the signal;

an event indicator device to generate an indication signal corresponding to an occurrence of an event; and a control unit coupled to the monitoring device and the event indicator device to determine a marginality in response to the indication signal and the sensed intervals, and determine the event as being one of the epileptic event and the syncope event in response to the determined marginality.

2. The medical device system of claim 1, wherein the control unit determines a first marginality corresponding to intervals sensed during a first time period including the generated indication signal and a second marginality corresponding to intervals sensed during a second time period preceding the generated indication signal, and compares the first marginality and the second marginality to determine the event.

3. The medical device system of claim 2, wherein the control unit determines a maximum marginality corresponding to the first time period and compares the second marginality to the maximum marginality.

4. The medical device system of claim 3, wherein the control unit determines the event as being the epileptic event in response to the second marginality being greater than the maximum marginality.

5. The medical device system of claim 3, wherein the control unit determines the event as being the syncope event in response to the second marginality not being greater than the maximum marginality.

6. The medical device system of claim 3, wherein the control unit determines the event as being the epileptic event in response to the second marginality being greater than the maximum marginality, and determines the event as being the syncope event in response to the second marginality not being greater than the maximum marginality.

7. The medical device system of claim 3, wherein the control unit determines the event as being the epileptic event in response to a sum of the second marginality and a predetermined threshold being greater than the maximum marginality, and determines the event as being the syncope event in response to the sum of the second marginality and the predetermined threshold not being greater than the maximum marginality.

8. The medical device system of claim 1, wherein the control unit determines marginalities corresponding to intervals sensed during a time period including the generated indication signal, determines a maximum marginality of the determined marginalities, compares the maximum marginality to a threshold, and determines the event as being one of the epileptic event and the syncope event in response to the comparing.

9. The medical device system of claim 8, wherein the monitoring device determines the event as being the epileptic event in response to the maximum marginality being greater than the threshold, and determines the event as being the syncope event in response to the maximum marginality not being greater than the threshold.

10. The medical device system of claim 1, further comprising an electrode coupled to the monitoring device, wherein the monitoring device senses the signal via the electrode, and wherein the electrode is positioned intravascularly within a patient.

11. The medical device system of claim 1, wherein the monitoring device comprises one of an implantable stimulator, an implantable monitor, or an external monitor.

12. A method of distinguishing an epileptic event from a syncope event in a medical device, comprising:

sensing a signal in the medical device;
generating sensed intervals in the medical device in response to the sensed signal;
generating an indication signal in the medical device in response to an occurrence of an event;
determining a marginality in the medical device in response to the generated indication signal and the sensed intervals; and
determining the event as being one of the epileptic event and the syncope event in the medical device in response to the determined marginality.

13. The method of claim 12, wherein determining a marginality comprises:
determining a first marginality corresponding to intervals sensed during a first time period including the generated indication signal; and
determining a second marginality corresponding to intervals sensed during a second time period preceding the generated indication signal, and wherein determining the event as being one of the epileptic event and the syncope event comprises comparing the first marginality and the second marginality.

14. The method of claim 13, further comprising determining a maximum marginality corresponding to the first time period in the medical device, and wherein determining the event as being one of the epileptic event and the syncope event comprises comparing the second marginality to the maximum marginality.

15. The method of claim 14, wherein determining the event as being one of the epileptic event and the syncope event comprises determining the event as being the epileptic event in response to the second marginality being greater than the maximum marginality.

16. The method of claim 14, wherein determining the event as being one of the epileptic event and the syncope event comprises determining the event as being the syncope event in response to the second marginality not being greater than the maximum marginality.

17. The method of claim 14, wherein determining the event as being one of the epileptic event and the syncope event comprises:
determining the event as being the epileptic event in response to a sum of the second marginality and a predetermined threshold being greater than the maximum marginality; and
determining the event as being the syncope event in response to the sum of the second marginality and the predetermined threshold not being greater than the maximum marginality.

18. The method of claim 12, further comprising:
determining, in the medical device, marginalities corresponding to intervals sensed during a time period including the generated indication signal;
determining, in the medical device, a maximum marginality of the determined marginalities;
comparing, in the medical device, the maximum marginality to a threshold; and
determining, in the medical device, the event as being one of the epileptic event and the syncope event in response to the comparing.

19. The method of claim 18, further comprising:
determining, in the medical device, the event as being the epileptic event in response to the maximum marginality being greater then the threshold; and
determining, in the medical device, the event as being the syncope event in response to the maximum marginality not being greater then the threshold.

20. The method of claim 12, further comprising sensing the signal via an electrode positioned intravascularly within a patient.

21. A non-transitory computer readable medium having computer executable instructions for performing a method in a medical device, the method comprising:
sensing a signal;
generating sensed intervals in response to the sensed signal;
generating an indication signal in response to an occurrence of an event;
determining a marginality in response to the generated indication signal and the sensed intervals; and
determining the event as being one of an epileptic event and a syncope event in response to the determined marginality.

22. The computer readable medium of claim 21, wherein determining a marginality comprises:
determining a first marginality corresponding to intervals sensed during a first time period including the generated indication signal; and
determining a second marginality corresponding to intervals sensed during a second time period preceding the generated indication signal, and wherein determining the event as being one of the epileptic event and the syncope event comprises comparing the first marginality and the second marginality.

23. The computer readable medium of claim 21, wherein determining a marginality comprises:
determining marginalities corresponding to intervals sensed during a time period including the generated indication signal;
determining a maximum marginality of the determined marginalities;
comparing the maximum marginality to a threshold; and
determining the event as being one of the epileptic event and the syncope event in response to the comparing.

* * * * *